United States Patent [19]

Smigel

[11] 4,405,599
[45] Sep. 20, 1983

[54] TOOTHPASTE FOR NATURAL TEETH AS WELL AS COMPOSITE FILLING MATERIAL

[76] Inventor: Irwin E. Smigel, 140 E. 72nd St., New York, N.Y. 10021

[21] Appl. No.: 395,846

[22] Filed: Jul. 6, 1982

[51] Int. Cl.$^3$ ............................................. A61K 7/20
[52] U.S. Cl. ..................... 424/53; 424/49; 424/57
[58] Field of Search ................... 424/53, 57

[56] References Cited

U.S. PATENT DOCUMENTS

| | | | |
|---|---|---|---|
| 1,018,240 | 2/1912 | Von Furegger | 424/53 |
| 1,863,116 | 6/1932 | Heymann | 424/53 |
| 2,052,694 | 9/1936 | Breivogez | 424/53 |
| 2,071,043 | 2/1937 | Nitardy | 424/53 |
| 2,090,437 | 8/1937 | Woldman | 424/53 |
| 2,094,671 | 10/1937 | Poetschke | 424/53 |
| 2,501,145 | 3/1950 | Smith | 424/53 |
| 3,936,385 | 2/1976 | Cheng | 424/53 |
| 3,988,433 | 10/1976 | Benedict | 424/53 |
| 4,062,793 | 12/1977 | Schodel | 424/53 |

FOREIGN PATENT DOCUMENTS 2085937 10/1980 United Kingdom .

*Primary Examiner*—Shep K. Rose
*Attorney, Agent, or Firm*—Hane, Roberts, Spiecens & Cohen

[57] ABSTRACT

A toothpaste composition adapted for cleaning natural teeth as well as composite filling material consisting essentially of, in percent by weight:
  Dicalcium Phosphate: 1.0% to 50%
  Calcium Carbonate: 1.0% to 50%
  Magnesium Carbonate: 1.0% to 25%
  Sorbitol 70%: 1.0% to 50%
  Cornstarch: 0.5% to 10%
  Cellulose Gum: 0.5% to 5.0%
  Calcium Peroxide: 0.5% to 5%
  Sodium Perborate: 0.5% to 5%
  Lathanol LAL: 0.1% to 5%
  Aluminum Hydroxide: 0.01 to 1%
  Sodium Saccharinate: 0.05% to 2%
  Peppermint Oil: 0.05% to 2%
  Methylparaben: 0.05% to 1.0%
  Denionized Water: 10% to 50%

7 Claims, No Drawings

TOOTHPASTE FOR NATURAL TEETH AS WELL AS COMPOSITE FILLING MATERIAL

FIELD OF THE INVENTION

The invention relates to a toothpaste composition—and particularly to such a composition adapted not only for cleaning natural teeth, but composite filling material as well.

BACKGROUND

In filling cavities from which dental caries have been removed, it has become an increasing practice to employ composite filling material which is similar in color to that of natural tooth material.

Such composite filling material is generally composed of a resinous substance which is polymerized in situ and which provides a hard bearing surface which has the natural appearance of a normal tooth.

Unfortunately, the composite filling material has inherent porosity and is relatively easily stained.

In a normal mouth, a salivary protein pellicle envelopes the tooth and is subject to plaque accumulation. Oral hygiene dictates the removal of the plaque accumulation in order to prevent decay of the tooth structure as well as serious diseases of the gums.

SUMMARY OF THE INVENTION

An object of the invention is to provide a toothpaste which is adapted for cleaning natural teeth as well as bonded composite filling material.

A further object of the invention is to provide a toothpaste which is specifically addressed to the removal of stain from composite filling material as well as from the tooth itself.

Another object of the invention is to provide a toothpaste composition which will be effective to remove the protein pellicles which normally envelope the teeth as well as plaque accumulation.

Yet another object of the invention is to provide a toothpaste of the above type which leaves the teeth with a smooth and clean feel.

Still another object of the invention is to provide a toothpaste composition of the above character which is effective for removing stains from natural teeth and composite filling material by means of a delicate balance of its ingredients without being abrasive.

In order to satisfy the above and further objects of the invention, there is provided a toothpaste according to the invention consisting essentially of the following ingredients in percent, by weight:

Dicalcium Phosphate: From 1.0% to 50%
Calcium Carbonate: From 1.0% to 50%
Magnesium Carbonate: From 1.0% to 25%
Sorbital 70%: From 1.0% to 50%
Corn Starch: From 0.5% to 10%
Cellulose Gum: From 0.5% to 5.0%
Calcium Peroxide: From 0.5% to 5%
Sodium Perborate: From 0.5% to 5%
Lathanol LAL (Sodium Lauryl Sulfoacetate): From 0.1% to 5%
Aluminum Hydroxide: From 0.01% to 1%
Saccharinate (Sodium Salt): From 0.05% to 2%
Peppermint Supra: From 0.05% to 2%
Methylparaben: From 0.05% to 1.0%
Deionized Water: From 10% to 50%

In the ingredients which have been listed above, there are nine active constituents which are present in a carefully balanced combination to achieve the objects of the invention. These consist of Dicalcium Phosphate, Calcium Carbonate, Magnesium Carbonate, Sorbitol, Cornstarch, Cellulose Gum, Calcium Peroxide, Sodium Perborate and Lathanol LAL. The invention covers these ingredients as well as their obvious equivalents.

The dicalcium phosphate, calcium carbonate and magnesium carbonate are cleaning agents.

The Sorbitol is a humectant.

The cornstarch and cellulose gum are thickening agents.

The calcium peroxide and sodium perborate are oxidizing agents.

The Lathanol is a detergent.

The Aluminum Hydroxide is a PH adjuster and is present in an amount to provide the composition with a substantially neutral PH.

The Saccharinate and Peppermint are present as taste ingredients and can be varied according to the desired taste to be provided for the composition.

The Methylparaben is a preservative and is one of various paraben compositions capable of acting as a preservative.

The Deionized Water is present in a amount to confer a suitable wetness for the composition in accordance to the desired viscosity of the composition.

DESCRIPTION OF PREFERRED EMBODIMENTS

One of the most important advances in dentistry in the past twenty-five years has been the development of the composite (tooth colored) restoration. This has revolutionized the profession from an esthetic concept. Composite filling material in conjunction with the evolution of light activation with its capability of controlling setting time and the dentist's ability to etch the enamel of teeth and thus bond the composite material directly onto the tooth is known as bonding. Bonding enables the dentist to close spaces between teeth, repair chips in teeth, cover discolorations and reshape abnormally shaped teeth. This coupled with the imminent development of composites for chewing surfaces of posterior teeth is expected to make the composite filling material the overwhelming material of choice in dentistry. However, the composite material for all of its advantages is inherently porous and is subject to staining. There are two types of composite filling material:

A. The conventional material which is composed of 76% inorganic filler material, such as quartz or Barium glass and 24% Resin Matrix, such as BIS GMA which is the reactive product of BIS Phenol A and Glycidyl Methyl acrylic.

B. Microfill—composed of 35-55% inorganic filler—such as fumed silica and 45-65% Resin Matrix, generally BIS GMA.

The present invention provides for a toothpaste composition which is capable of cleaning natural teeth as well as the composite filling material.

The invention provides a toothpaste composition which will satisfy the above and which has a specific balance of active ingredients to clean natural teeth as well as composite filling material. This composition consists of the following ingredients, given in percent by weight:

| INGREDIENT | AMOUNT IN % |
|---|---|
| Dicalcium Phosphate | 15 |
| Calcium Carbonate | 15 |
| Magnesium Carbonate | 12 |
| Sorbitol 70% | 15 |
| Cornstarch | 2 |
| Cellulose Gum | 2 |
| Calcium Peroxide | 1 |
| Sodium Perborate | 1 |
| Lathanol LAL (Sodium Lauryl Sulfoacetate) | 0.8 |
| Aluminum Hydroxide | 0.6 |
| Saccarinate (Sodium Salt) | 1 |
| Peppermint Supra | 1 |
| Methylparaben (Hydrozybenzoic acid methyl ester) | 0.1 |
| Deionized Water | 33.5 |

The above composition had the paste-like texture of standard toothpaste and was found to be exceptionally effective in its ability to remove stains and plaque from normal teeth as well as composite filling material.

The toothpaste composition was prepared in conventional manner as a mixture of the various ingredients.

While the invention has been described in connection with a single embodiment thereof, it will become apparent to those skilled in the art that various equivalents may be used within the scope and spirit of the invention as defined by the attached claims.

What is claimed is:

1. A toothpaste composition consisting essentially of, in percent by weight:
   Dicalcium Phosphate: 1.0% to 50%
   Sorbital 70%: 1.0% to 50%
   Cornstarch: 0.5% to 10%
   Cellulose Gum: 0.5% to 5.0%
   Calcium Peroxide: 0.5% to 5%
   Sodium Perborate: 0.5% to 5%
   Lathanol LAL: 0.1% to 5%
   Aluminum Hydroxide: 0.01% to 1%.

2. A toothpaste composition as claimed in claim 1 further including a preservative.

3. A toothpaste composition as claimed in claim 2 wherein the preservative is an alkyl paraben in an amount from 0.05% to 1%.

4. A toothpaste composition as claimed in claim 1 further including taste ingredients.

5. A toothpaste composition as claimed in claim 4 wherein said taste ingredients include a sweetening agent in an amount from 0.05% to 2% and a flavoring ingredient in an amount from 0.05% to 2%.

6. A toothpaste composition as claimed in claim 1 further including a PH adjustment ingredient to render the toothpaste composition substantially PH neutral.

7. A toothpaste composition as claimed in claim 1 wherein the water is present in the amount of from 10 to 50%.